(12) United States Patent
Fukasawa

(10) Patent No.: US 11,172,898 B2
(45) Date of Patent: Nov. 16, 2021

(54) RADIATION IMAGING SYSTEM, RADIATION CONTROL APPARATUS AND METHOD OF CONTROLLING RADIATION IMAGING SYSTEM

(71) Applicant: CANON KABUSHIKI KAISHA, Tokyo (JP)

(72) Inventor: Taro Fukasawa, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 16/844,056

(22) Filed: Apr. 9, 2020

(65) Prior Publication Data
US 2020/0337660 A1 Oct. 29, 2020

(30) Foreign Application Priority Data

Apr. 25, 2019 (JP) .............................. JP2019-084428

(51) Int. Cl.
*A61B 6/00* (2006.01)
*G01T 1/17* (2006.01)
*H04N 5/32* (2006.01)

(52) U.S. Cl.
CPC ................ *A61B 6/484* (2013.01); *G01T 1/17* (2013.01); *H04N 5/32* (2013.01); *A61B 6/542* (2013.01)

(58) Field of Classification Search
CPC ........... A61B 6/484; A61B 6/542; G01T 1/17; H04N 5/32
See application file for complete search history.

(56) References Cited

U.S. PATENT DOCUMENTS

| 2008/0152088 A1* | 6/2008 | Wang | G03B 42/02 378/98.12 |
| 2009/0123051 A1* | 5/2009 | Tamai | A61B 6/542 382/132 |
| 2009/0201841 A1* | 8/2009 | Tachikawa | H04L 12/413 370/310 |

(Continued)

FOREIGN PATENT DOCUMENTS

| JP | 2015-136546 A | 7/2015 |
| JP | 2016-097115 | 5/2016 |

(Continued)

OTHER PUBLICATIONS

European Search Report dated Oct. 7, 2020 in counter part application EP 20168394.3.

*Primary Examiner* — Blake C Riddick
(74) *Attorney, Agent, or Firm* — Venable LLP

(57) ABSTRACT

A radiation imaging system is provided. The radiation imaging system comprises an irradiation control apparatus configured to control a timing of radiation irradiation by a radiation generating apparatus and a radiation imaging apparatus configured to communicate by at least one synchronous communication method to synchronize with the radiation irradiation. The irradiation control apparatus comprises a determination unit configured to determine an imaging mode that has been set and a synchronous communication method which can be supported by the radiation imaging apparatus, and a control unit configured to control, based on the determination result, the timing of the radiation irradiation by a synchronous communication method corresponding to the imaging mode.

11 Claims, 6 Drawing Sheets

(56) References Cited

U.S. PATENT DOCUMENTS

| | | | | |
|---|---|---|---|---|
| 2010/0078583 | A1* | 4/2010 | Tsubota | A61B 6/548 250/580 |
| 2011/0110497 | A1* | 5/2011 | Nishino | A61B 6/542 378/98.8 |
| 2011/0158385 | A1* | 6/2011 | Nakatsugawa | A61B 6/548 378/44 |
| 2011/0170669 | A1* | 7/2011 | Nakatsugawa | A61B 6/56 378/116 |
| 2012/0018640 | A1* | 1/2012 | Shimizukawa | A61B 6/4233 250/354.1 |
| 2012/0201351 | A1* | 8/2012 | Iwakiri | A61B 6/545 378/62 |
| 2013/0168558 | A1* | 7/2013 | Tsuchiya | A61B 6/54 250/363.01 |
| 2013/0230141 | A1* | 9/2013 | Miyachi | G01N 23/04 378/62 |
| 2013/0279657 | A1* | 10/2013 | Hiroike | A61B 6/4241 378/62 |
| 2013/0279661 | A1* | 10/2013 | Tamura | A61B 6/4208 378/98 |
| 2014/0086391 | A1* | 3/2014 | Ohta | H04N 5/2351 378/91 |
| 2014/0254758 | A1* | 9/2014 | Saigusa | A61B 6/545 378/62 |
| 2014/0254759 | A1 | 9/2014 | Haraguchi | |
| 2014/0254765 | A1* | 9/2014 | Asai | A61B 6/5258 378/98.5 |
| 2014/0295767 | A1* | 10/2014 | Iijima | A61B 6/56 455/41.3 |
| 2016/0029986 | A1* | 2/2016 | Nishii | A61B 6/4233 250/394 |
| 2016/0131772 | A1 | 5/2016 | Sato | |
| 2016/0228087 | A1* | 8/2016 | Oda | A61B 6/465 |
| 2017/0014094 | A1* | 1/2017 | Hiroshige | H04N 5/361 |
| 2017/0153333 | A1* | 6/2017 | Morita | G01T 1/247 |
| 2018/0106914 | A1 | 4/2018 | Morita et al. | |
| 2020/0037426 | A1 | 1/2020 | Uchiyama | |

FOREIGN PATENT DOCUMENTS

| | | |
|---|---|---|
| JP | 2018-175125 | 11/2018 |
| JP | 2018-192024 | 12/2018 |

* cited by examiner

RADIATION IMAGING SYSTEM, RADIATION CONTROL APPARATUS AND METHOD OF CONTROLLING RADIATION IMAGING SYSTEM

BACKGROUND OF THE INVENTION

Field of the Invention

The present invention relates to a radiation imaging system, a radiation control apparatus and a method of controlling the radiation imaging system.

Description of the Related Art

Conventionally, there is commercially available a radiation imaging apparatus and a radiation imaging system that obtain a sharp radiation image by irradiating an object with radiation from a radiation generating apparatus, digitizing the intensity distribution of radiation transmitted through the object, and executing image processing on the digitized radiation image.

In such a radiation imaging apparatus, a two-dimensional solid-state image sensor is generally used as a radiation detector. The radiation detector operates by converting radiation into charges, accumulating the charges in a capacitor, and repeating a readout operation and a reset operation of the accumulated charges. In an image sensor that does not include an electronic shutter, if the image sensor is irradiated with radiation when a charge readout operation or a reset operation is being performed, charges unrelated to the radiation imaging will be superimposed on the obtained radiation image, and the image quality of the radiation image will degrade.

Hence, synchronization between the operation timing of the radiation detector of the radiation imaging apparatus and the irradiation timing of the radiation generating apparatus is required in the radiation imaging system.

Japanese Patent Laid-Open No. 2016-97115 discloses an arrangement in which imaging is performed by using wireless communication to execute communication between a radiation imaging apparatus and a radiation generating apparatus for each imaging operation. Also, Japanese Patent Laid-Open No. 2018-175125 discloses a radiation imaging system that includes a control apparatus of a radiation generating apparatus, which includes a first time count unit, and a radiation imaging apparatus, which includes a second time count unit that is synchronized with the first time count unit.

In the system disclosed in Japanese Patent Laid-Open No. 2016-97115, communication via packet communication is performed sequentially between the radiation imaging apparatus and the radiation generating apparatus for each imaging operation. However, the order of the packets is arbitrary, and retransmission processing or the like becomes necessary in a case in which information transmission is determined to be difficult in the wireless communication environment. Thus, it is difficult to perform an accurate synchronous imaging operation when a high frame rate moving image is to be captured.

Also, in the system disclosed in Japanese Patent Laid-Open No. 2018-175125, synchronization between radiation irradiation and the operation of the imaging apparatus can be performed by wireless communication using a network line when a high frame rate moving image is to be captured. However, time inquiry communication between the apparatuses need to be performed constantly to continuously maintain the synchronization between the radiation generating apparatus and the radiation imaging apparatus, both including internal timers. Thus, in still image capturing, since it is sufficient to perform synchronous communication at the start of the imaging operation, constant performance of time inquiry communication is excessive communication, and the power consumption will increase more than necessary.

In consideration of the above problems, the present invention provides a radiation imaging technique that allows radiation irradiation timing to be controlled by a synchronous communication method corresponding to an imaging mode.

SUMMARY OF THE INVENTION

According to one aspect of the present invention, there is provided a radiation imaging system comprising an irradiation control apparatus configured to control a timing of radiation irradiation by a radiation generating apparatus and a radiation imaging apparatus configured to communicate by at least one synchronous communication method to synchronize with the radiation irradiation, the irradiation control apparatus comprising a determination unit configured to determine an imaging mode that has been set and a synchronous communication method which can be supported by the radiation imaging apparatus, and a control unit configured to control, based on the determination result, the timing of the radiation irradiation by a synchronous communication method corresponding to the imaging mode.

According to another aspect of the present invention, there is provided a radiation control apparatus configured to control a timing of radiation irradiation by a radiation generating apparatus and to communicate with a radiation imaging apparatus by at least one synchronous communication method to synchronize with the radiation irradiation comprising; a determination unit configured to determine an imaging mode that has been set and a synchronous communication method which can be supported by the radiation imaging apparatus, and a control unit configured to control, based on the determination result, the timing of the radiation irradiation by a synchronous communication method corresponding to the imaging mode.

According to still another aspect of the present invention, there is provided a method of controlling a radiation imaging system that comprises an irradiation control apparatus configured to control the timing of radiation irradiation by a radiation generating apparatus and a radiation imaging apparatus configured to communicate by at least one synchronous communication method to synchronize with the radiation irradiation, the method comprising, in the irradiation control apparatus, determining an imaging mode that has been set and a synchronous communication method which can be supported by the radiation imaging apparatus, and controlling, based on a result from the determining, the timing of the radiation irradiation by a synchronous communication method corresponding to the imaging mode.

Further features of the present invention will become apparent from the following description of exemplary embodiments (with reference to the attached drawings).

DESCRIPTION OF THE EMBODIMENTS

Figure 1:
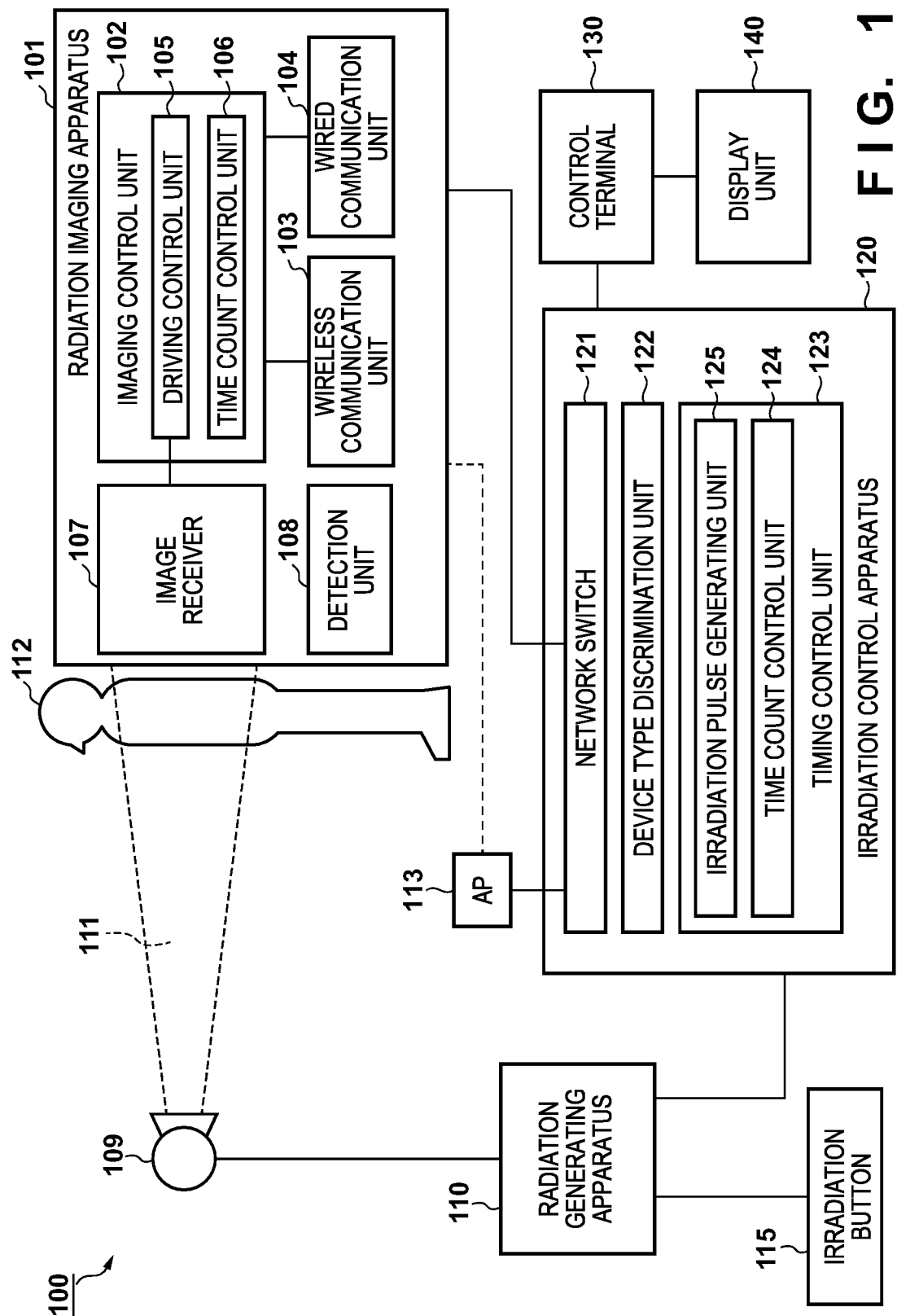
FIG. 1 is a view showing an example of the arrangement of a radiation imaging system according to an embodiment.

Hereinafter, embodiments will be described in detail with reference to the attached drawings. Note, the following embodiments are not intended to limit the scope of the claimed invention. Multiple features are described in the embodiments, but limitation is not made an invention that requires all such features, and multiple such features may be combined as appropriate. Furthermore, in the attached drawings, the same reference numerals are given to the same or similar configurations, and redundant description thereof is omitted.

In the following embodiments and the appended claims, radiation includes, in addition to X-rays, α-rays, β-rays, γ-rays, and various kinds of particle beams.

(System Arrangement)

FIG. 1 is a view showing an example of the arrangement of a radiation imaging system 100 according to an embodiment of the present invention. The radiation imaging system 100 includes a radiation generating apparatus 110, an irradiation control apparatus 120 that controls the timing of radiation irradiation by the radiation generating apparatus 110, a radiation imaging apparatus 101 that can communicate by at least one synchronous communication method to synchronize with the radiation irradiation operation, and a control terminal 130. In the radiation imaging system 100 shown in FIG. 1, synchronous communication related to the radiation irradiation timing can be performed between the radiation imaging apparatus 101 and the radiation generating apparatus 110 by using wired communication or wireless communication.

An operator can use the control terminal 130 and a display unit 140 to set operation conditions of the system. The information of the set operation conditions is transmitted to the irradiation control apparatus 120, and the information is transmitted from the irradiation control apparatus 120 to the radiation imaging apparatus 101 and the radiation generating apparatus 110. A message related to the start of an imaging operation is exchanged between the irradiation control apparatus 120 and the radiation imaging apparatus 101 when an irradiation button 115 is pressed, and the radiation generating apparatus 110 subsequently emits radiation. The radiation emitted from the radiation generating apparatus 110 is captured by the radiation imaging apparatus 101 after passing through an object 112.

The irradiation control apparatus 120 includes a network switch 121 that functions as a communication unit, a device type discrimination unit 122 (determination unit) that discriminates the device type of the radiation imaging apparatus 101, and a timing control unit 123. In this case, the device type discrimination unit 122 determines, based on identification information, the set imaging mode (moving image capturing or still image capturing) and a synchronous communication method (to be also simply referred to as a synchronization method hereinafter) that corresponds to the radiation imaging apparatus 101. The timing control unit 123 can control, based on the determination result of the device type discrimination unit 122, the radiation irradiation timing by the synchronous communication method corresponding to the imaging mode, and includes, as functional components, a time count control unit 124 and an irradiation pulse generating unit 125. The timing control unit 123 switches the communication with the radiation imaging apparatus 101 based on the determination result of the device type discrimination unit 122.

By exchanging messages with the radiation imaging apparatus 101 (time client), the network switch 121 (communication unit) transmits time information of an internal timer included in the time count control unit 124. At the time of imaging, when the exchanging of messages related to the start of imaging has been completed with the radiation imaging apparatus 101, the irradiation control apparatus 120 transmits, to the radiation generating apparatus 110, a signal (control signal) for radiation irradiation timing control that has been generated by the irradiation pulse generating unit 125 based on the time information of the time count control unit 124 as a reference.

The radiation generating apparatus 110 includes a light tube and an exposure field aperture mechanism. The radiation generating apparatus 110 generates radiation continuously or in pulses by a predetermined tube voltage or tube current based the control signal received from the irradiation control apparatus 120. The radiation generated by the radiation generating apparatus 110 is emitted from a radiation source 109, and the emitted radiation is captured by the radiation imaging apparatus 101 which is synchronized with the irradiation timing.

The radiation imaging apparatus 101 is an apparatus that obtains radiation image data of the object 112 based on radiation 111 emitted from the radiation source 109 and transmitted through the object 112, and, for example, a radiation imaging apparatus using a flat panel detector (FPD) or the like can be used. The radiation imaging apparatus 101 includes an image receiver 107 (imaging unit) on which pixels for converting radiation into an electrical signal are two-dimensionally arranged to generate captured image data corresponding to the received radiation, a detection unit 108 that detects radiation irradiation, an imaging control unit 102, and a wired communication unit 104 as a component of a communication unit. The imaging control unit 102 includes a driving control unit 105 and a time count control unit 106, and the wired communication unit 104 is connected to the network switch 121 of the irradiation control apparatus 120.

The radiation imaging apparatus 101 can also include, as a component of the communication unit, a wireless communication unit 103, and use an access point (AP) 113 of wireless communication (wireless LAN) included as a part of a network infrastructure to connect a partial section between the wireless communication unit 103 and the network switch 121 by wireless communication.

Information can be exchanged in the form of messages between devices which are connected (wirelessly connected) via a network. In contrast, the connection between the radiation generating apparatus 110 and the timing control unit 123 of the irradiation control apparatus 120 is by direction connection (wired connection) without the intervention of the network, and a signal is electrically transmitted directly without being converted into a message.

For example, pixels that include photoelectric conversion elements and switch elements such as a TFT are arranged two-dimensionally (for example, in a two-dimensional array) in the image receiver 107, and a fluorescent material that converts radiation into visible light is arranged on, for example, each photoelectric conversion element. Radiation that enters the image receiver 107 is converted into visible light by the fluorescent material, the converted visible light enters the photoelectric conversion element of each pixel, and charges (electrical signal) corresponding to the visible light are generated as radiation image data in each photoelectric conversion element.

The imaging control unit 102 performs processing related to driving control of the image receiver 107, various kinds of image processing with respect to captured radiation image data, storage of the radiation image data, determination of the transfer timing of the radiation image data, transfer control of the radiation image data, and the like.

The driving control unit 105 of the imaging control unit 102 performs driving control of the image receiver 107. The time count control unit 106 of the imaging control unit 102 is used to synchronize the driving timing of the image receiver 107 with the radiation irradiation timing (to be described later). The time count control unit 106 includes an internal timer, corrects the time of the internal timer with the irradiation control apparatus 120, and controls the driving timing of the image receiver 107 based on the time information of the internal timer. The image data processed by the imaging control unit 102 is transferred from the irradiation control apparatus 120 to the control terminal 130 via the wired communication unit 104 and the network switch 121, and the image data is displayed on the display unit 140 to be provided for inspection or the like.

In the radiation imaging system 100, time synchronization via the network or sequential synchronization of exchanging signals for each radiation irradiation timing and each imaging timing can be used as the synchronous communication method between the radiation imaging apparatus 101 and the radiation generating apparatus 110.

The radiation imaging system 100 can support moving image capturing and still image capturing. The device type of the radiation imaging apparatus 101 used in the radiation imaging system 100 is, for example, a device type that can capture a moving image and a still image or a device type that can capture at least one of a moving image and a still image, and the device type discrimination unit 122 in the irradiation control apparatus 120 can discriminate the device type of the radiation imaging apparatus 101. The device type discrimination unit 122 can identify the device type of the radiation imaging apparatus 101 based on the identification information obtained from the radiation imaging apparatus 101 via the network switch 121.

Identification information, which is about a few bits, has been preset to the radiation imaging apparatus 101 for each synchronization method that can be supported. For example, "001" is set as the identification information of a device type that is capable of supporting time synchronization, and "010" is set as the identification information of a device type that does not support time synchronization. Note that the identification information is not limited to time synchronization. Assume that identification information is set to sequential synchronization in a similar manner.

The device type discrimination unit 122 can obtain the identification information via the wireless communication unit 103 or the wired communication unit 104 and the network switch 121, and discriminate the synchronization method supported by the radiation imaging apparatus 101 (the device type of the radiation imaging apparatus 101) for data communication.

The irradiation control apparatus 120 may also obtain the identification information by connecting to hardware such as a relay apparatus or the like. A relay apparatus is an apparatus that converts mutually different interfaces to connect the interfaces to each other. For example, a relay apparatus or the like that has an interface conversion function can be used to connect the radiation imaging apparatus 101 and the irradiation control apparatus 120. By setting the identification information of the radiation imaging apparatus 101 to the relay apparatus, the compatibility (connection compatibility with an existing product) between the radiation imaging apparatus 101 and the irradiation control apparatus 120 can be ensured by the interface conversion function of the relay apparatus, in addition to the device type discrimination of the radiation imaging apparatus 101, when the apparatuses are to be connected. Since the connection compatibility can be ensured, it becomes possible to provide a highly convenient radiation imaging technique.

(Synchronous Communication Methods)

Time synchronization and sequential synchronization as synchronous communication methods that can be applied to the radiation imaging system 100 will be described next. In time synchronization, communication is performed to set the times of the respective internal timers included in the irradiation control apparatus 120 and the radiation imaging apparatus 101. In sequential synchronization, after the radiation imaging apparatus 101 has completed the imaging preparation in response to an imaging request from the irradiation control apparatus 120, the timing control unit 123 of the irradiation control apparatus 120 outputs an imaging permission which allows radiation irradiation to be performed. The timing control unit 123 controls the radiation irradiation timing by time synchronization when performing moving image capturing, and controls the radiation irradiation timing by sequential synchronization when performing still image capturing.

In a medical facility, each apparatus tends to be installed in separate rooms, for example, the radiation imaging apparatus 101 that forms the radiation imaging system 100 is installed in an inspection room, the irradiation control apparatus 120 is installed in an equipment room, the control terminal 130 is installed in an anteroom, and the like. Hence, the apparatuses are connected to each other via a network like such as a wireless LAN and a wired LAN which is capable of long distance transmission.

In still image capturing, the radiation generating apparatus 110 and the radiation imaging apparatus 101 exchange, on the network via the network switch 121 of the irradiation control apparatus 120 and the wireless communication unit 103 or the wired communication unit 104 of the radiation imaging apparatus 101, signals indicating the completion of imaging preparation and the start/end of radiation irradiation to perform imaging by sequentially synchronizing an operation for radiation generation and an operation for radiation detection and charge accumulation (sequential synchronization).

In moving image capturing, since a period in which images of a single frame can be received is limited, if message retransmission processing or the like is to be performed due to an occurrence of a delay in message communication on the network line, it becomes difficult to achieve synchronization by exchanging messages frame by frame in the manner of sequential synchronization.

Hence, in moving image capturing, time synchronization of the internal timer included in the time count control unit 124 of the irradiation control apparatus 120 and the internal timer of the time count control unit 106 of the radiation imaging apparatus 101 is executed to perform imaging in accordance the completion of imaging preparation, the irradiation start time, the accumulation completion timing, and the irradiation completion timing (time synchronization).

Time synchronization is not limited to moving image capturing and is also applicable to still image capturing as long as it is used in a system using a network line. Since it is sufficient to synchronize the imaging timing and the irradiation timing in still image capturing, continuous time inquiry communication will lead to an excessive amount of communication, and the increase in the power consumption will increase heat generation. Hence, by synchronizing the imaging timing and the irradiation timing and subsequently executing control not to perform time inquiry communication in still image capturing, an excessive amount of communication can be suppressed, and heat generation can be suppressed.

Also, in still image capturing, since a cooling process or the like of the radiation imaging apparatus 101 is not generally performed, noise can be generated in an image due to unevenness caused by heat generation. However, by suppressing heating by reducing power consumption, noise generation due to the unevenness caused by the heat generation can be suppressed.

In time synchronization, the irradiation control apparatus 120 and the radiation imaging apparatus 101 need to be able to operate in correspondence with time synchronization. The radiation imaging system 100 according to this embodiment is a system that can perform both moving image capturing and still image capturing, and the synchronous communication method (time synchronization or sequential synchronization) can be selected based on the imaging mode or the device type discrimination result of the radiation imaging apparatus 101 by determining the imaging mode and discriminating the device type of the radiation imaging apparatus 101 to be connected.

(Time Synchronization)

The outline of a moving image capturing operation by time synchronization will be described with reference to FIGS. 1 and 2. First, before the imaging operation, parameters for moving image capturing such as the frame rate, the radiation pulse length per frame, and the like are set to the corresponding units of the radiation imaging system 100 in advance. The operator of the system presses the irradiation button 115 at a timing at which he/she desires to perform the imaging operation. The pressing of the irradiation button 115 is transmitted as an electrical signal to the timing control unit 123. Upon receiving the transmitted electrical signal, the timing control unit 123 generates a message indicating the start of imaging and exchanges the message with the radiation imaging apparatus 101 via the network. When the message exchange is completed, the irradiation pulse generating unit 125 of the timing control unit 123 generates a signal (a control signal: a timing pulse) for controlling the radiation irradiation timing.

The irradiation pulse generating unit 125 generates the control signal based on the time information of the internal timer held by the time count control unit 124 which is present in the timing control unit 123. The control signal generated by the irradiation pulse generating unit 125 is transmitted to the radiation generating apparatus 110. The radiation generating apparatus 110 generates radiation in accordance with the control signal transmitted from the irradiation pulse generating unit 125, and the radiation 111 is emitted from the radiation source 109.

On the other hand, in the radiation imaging apparatus 101, after the message exchange has ended, the driving control unit 105 of the imaging control unit 102 generates a driving control signal of the image receiver 107 to obtain radiation image data from the image receiver 107. At this time, the driving control unit 105 generates the driving control signal based on the time information of the internal timer held by the time count control unit 106 present in the radiation imaging apparatus 101. When the operator of the system stops pressing the irradiation button 115 to end the imaging operation, the timing control unit 123 stops the generation of the control signal (timing pulse), generates a message indicating that the imaging operation will be stopped, and exchanges the message with the radiation imaging apparatus 101.

In the operation described above, the processing to obtain radiation image data from the image receiver 107 is performed by selecting a time that does not overlap the radiation irradiation timing. That is, the obtainment of the radiation image data is performed in a time zone different from the time zone of the radiation irradiation operation. To execute this exclusive control, the time (the time of the internal timer) of the time count control unit 124 in the irradiation control apparatus 120 and the time (the time of the internal timer) of the time count control unit 106 in the radiation imaging apparatus 101 need to be in an accurately synchronized state.

Figure 2:
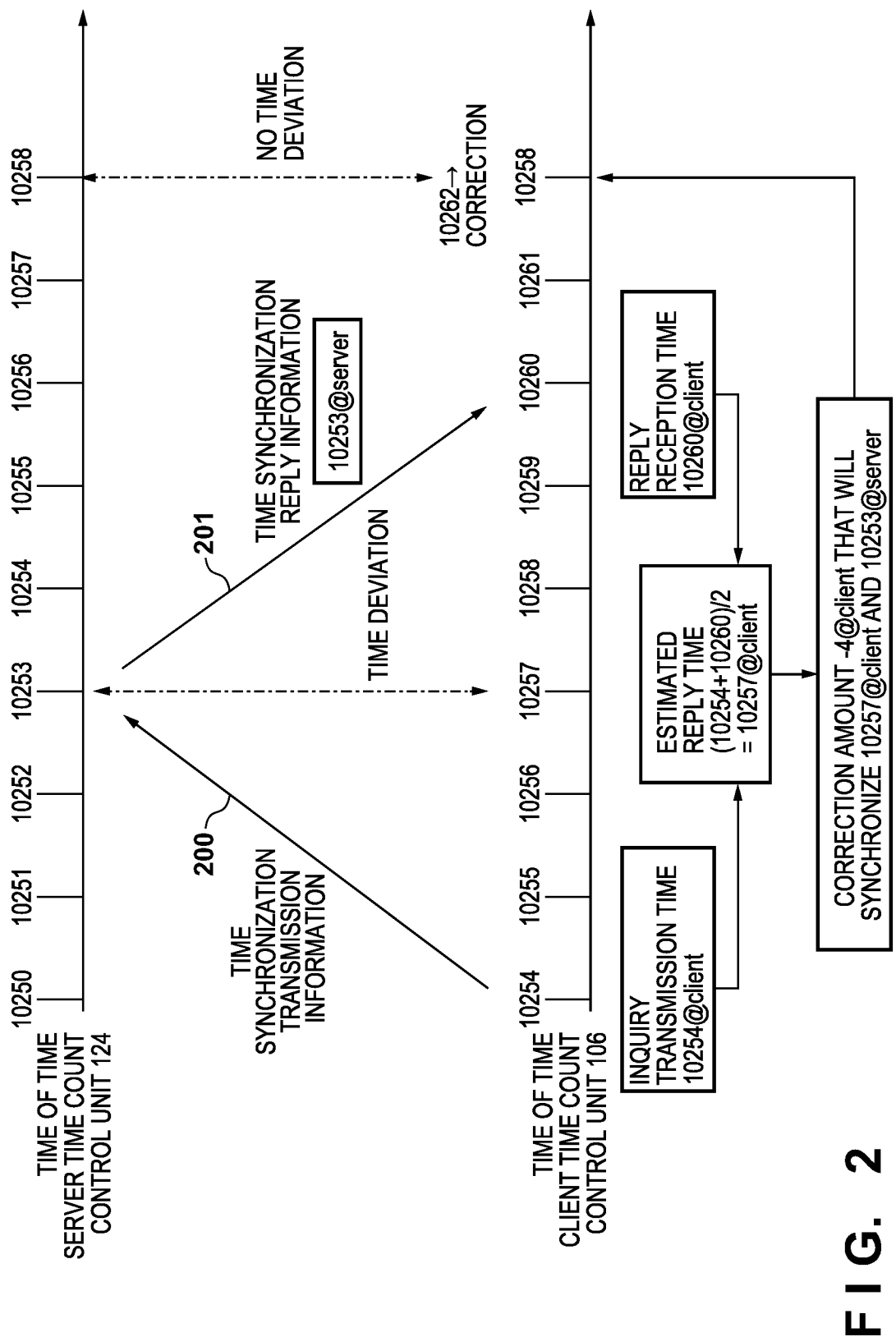
FIG. 2 is a view for explaining the processing procedure of time synchronization.

FIG. 2 is a view for explaining the processing procedure of time synchronization (time setting), and the procedure for synchronizing the time of the time count control unit 106 of the radiation imaging apparatus 101 and the time of the time count control unit 124 of the irradiation control apparatus 120 will be described with reference to FIG. 2. In the radiation imaging system 100, the irradiation control apparatus 120 (the time count control unit 124) operates as a time server, and the radiation imaging apparatus 101 (the time count control unit 106) operates as a time client, that is, operates in accordance with the time server.

First, the radiation imaging apparatus 101 transmits, through the communication unit (the wired communication unit 104 or the wireless communication unit 103), a time inquiry message (time synchronization transmission information 200) inquiring the time of the time server to the time count control unit 124. At this time, when the time count control unit 106 of the radiation imaging apparatus 101 is to transmit the message, the time information of the time count control unit 106 at the transmission time is stored in the time count control unit 106 and transmitted. For example, when the message is transmitted at a time value 10254 indicated by the timer held by the time count control unit 106, the time count control unit 106 stores the time value 10254 as the inquiry transmission time in its internal memory and transmits the message.

The irradiation control apparatus 120, which received the time inquiry message from the time count control unit 106 of the radiation imaging apparatus 101, transmits a time reply message (time synchronization reply information 201). That is, in the same manner as the time client, the time count control unit 124 of the irradiation control apparatus 120 transmits the time reply message to the time count control unit 106 via the network switch 121 or the wireless communication (wireless LAN) access point (AP) 113.

For example, if the time synchronization reply information 201 is transmitted at a time value 10253 indicated by the timer held in the time count control unit 124, the time count control unit 124 stores the time value 10253 as the reply transmission time in the time reply message (10253@server, "@server" indicates the time of the time server hereinafter) and transmits the message.

The radiation imaging apparatus 101 receives the time reply message transmitted from the irradiation control apparatus 120. At this time, the time reply message is obtained at the uncorrected time (reply reception time) held by the time count control unit 106 of the radiation imaging apparatus 101. For example, in FIG. 2, the time count control unit 106 obtains the time reply message at a time value 10260 and stores the value as the reply reception time in its internal memory.

If the communication times (propagation times) required for the communication of both the time inquiry message and the time reply message are assumed to be equal, the time (estimated reply time) at which the irradiation control apparatus 120 transmitted the time reply message can be estimated, based on the time of the timer held by the time count control unit 106, as a time at the midpoint between the inquiry transmission time 10254 (10254@client, "@client" indicates the time of the client hereinafter) and the reply reception time 10260 (10260@client).

That is, the time count control unit 106 can estimate the estimated reply time by the following averaging operation.

(10254+10260)/2=10257(10257@client)

To obtain the time deviation between the radiation imaging apparatus 101 and the irradiation control apparatus 120, the time count control unit 106 (client) obtains the difference between the estimated reply time of the time count control unit 106 and the reply transmission time of the irradiation control apparatus 120 (time server). That is, by obtaining a difference time (time difference) between the estimated reply time 10257@client and the reply transmission time 10253@server, the time count control unit 106 can understand that there is a time deviation between the two apparatuses and that the time of the radiation imaging apparatus 101 is ahead by 10257−10253=4. −4@client is the correction amount that will synchronize the time value 10257@client and the time value 10254@server.

The time count control unit 106 corrects, based on the obtained time difference, the time value of the timer included in the time count control unit 106 to synchronize the time of the time count control unit 106 and the time of the time count control unit 124.

The time count control unit 106 performs correction by subtracting the difference time (time difference) from the time information of the time count control unit 106 of the client so that the estimated reply time 10257 (10257@client) of the client and the reply transmission time 10253 (10253@server) of the time server will be the same time. That is, the time count control unit 106 corrects the time value of the timer by subtracting the correction amount −4@client from the time value 10262@client of the timer included in the time count control unit 106. The corrected time value is a time value 10258@client in FIG. 2, and this time value is the same as a time value 10258@server of the timer included in the time count control unit 124.

The time difference between the time count control unit 106 and the time count control unit 124 can be calculated by the above arithmetic processing, and the time count control unit 106 can correct the time information of the time count control unit 106 based on the calculated time difference. As a result, a state (time synchronization state) in which there is no time deviation between the radiation imaging apparatus 101 and the irradiation control apparatus 120 is set.

Although FIG. 2 described an example in which the time count control unit 124 of the irradiation control apparatus 120 is set as the time server and the time count control unit 106 of the radiation imaging apparatus 101 is set as the time client, the time count control unit 124 may function as the time client and the time count control unit 106 may function as the time server.

Also, in the example of FIG. 2, the estimated reply time is obtained based on a single inquiry made by using the combination of the time synchronization transmission information 200 and the time synchronization reply information 201 as a set, and a time correction value (time synchronization correction value) is determined from the difference time (time difference) between the estimated reply time and the inquiry transmission time. However, since the actual communication time (propagation time) can fluctuate, a time correction value that has been obtained based on a single inquiry can be a value that deviates from the real time. Hence, the time correction value can be calculated by executing a plurality of inquiries and statistically processing the time differences obtained in correspondence with the inquiries.

Various kinds of information can be transmitted through the network in the radiation imaging system. The above example has described, as the various kinds of information, the radiation image data, the messages exchanged to control the start and the end of imaging, the inquiry and reply for time synchronization, and the like. Other than these pieces of information, commands for transmitting the setting information in advance and messages for reporting the (abnormal or normal) states of the respective apparatuses can be transmitted via the network.

(Sequential Synchronization)

Figure 3:
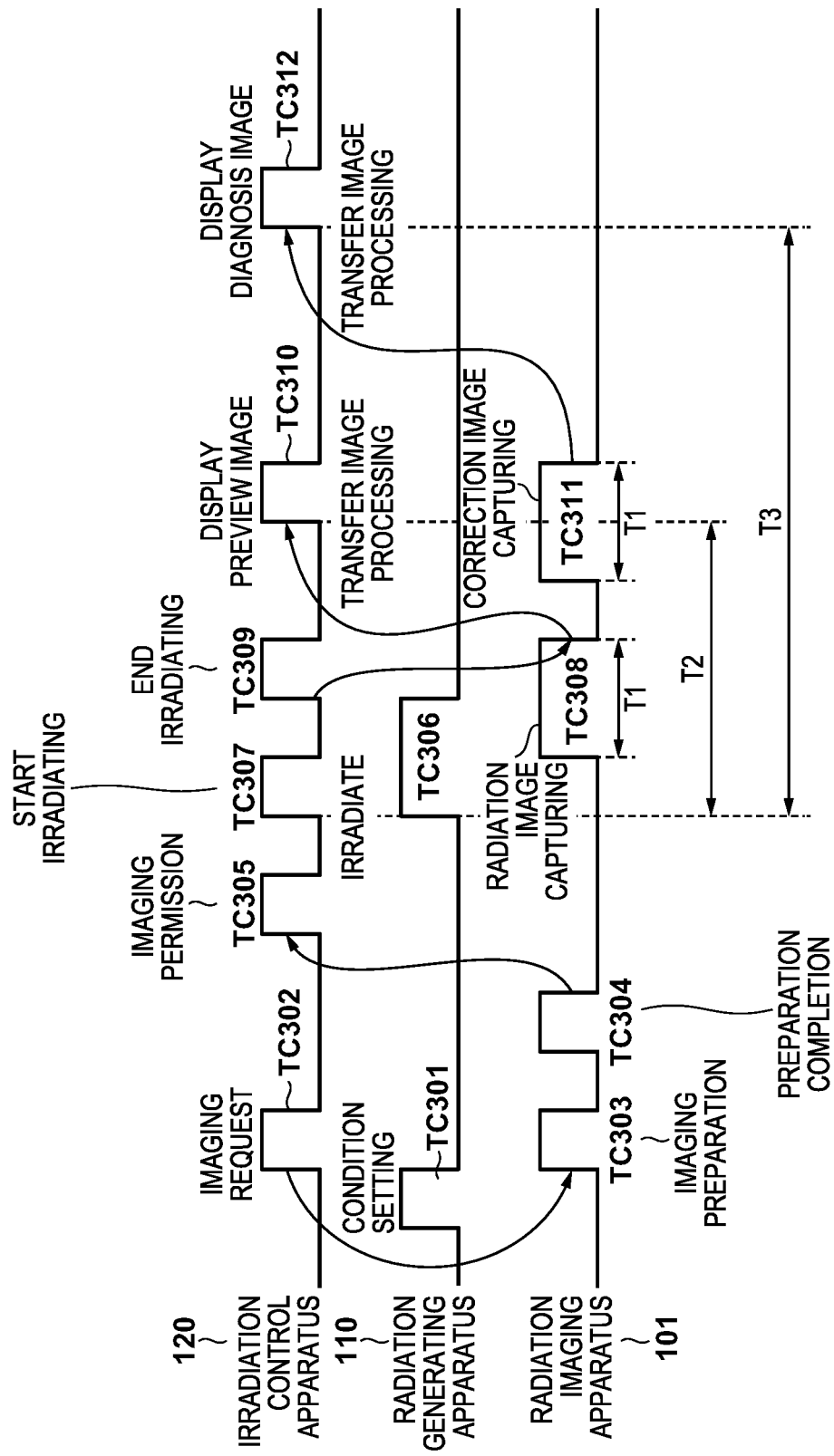
FIG. 3 is a timing chart for explaining the processing procedure of sequential synchronization.

FIG. 3 is a timing chart for explaining the processing procedure of sequential synchronization. The outline of an imaging operation by sequential synchronization will be described with reference to FIGS. 1 and 3. Sequential synchronization is a method of performing imaging by sequentially synchronizing the radiation generation operation and the radiation detection and charge accumulation operation by causing the radiation generating apparatus 110 and the radiation imaging apparatus 101 to exchange, on the network via the network switch 121 of the irradiation control apparatus 120 and the wireless communication unit 103 or the wired communication unit 104 of the radiation imaging apparatus 101, signals indicating the completion of imaging preparation and the start/end of radiation irradiation.

The operator can use the control terminal 130 and the display unit 140 to set operation conditions of the system. The condition setting information is transmitted to the irradiation control apparatus 120 and transmitted from the irradiation control apparatus 120 to the radiation imaging apparatus 101 and the radiation generating apparatus 110 (TC301). When an imaging request is input to the irradiation control apparatus 120 by the operation by the operator, a request signal based on the imaging request is transmitted from the irradiation control apparatus 120 to the radiation imaging apparatus 101 (TC302).

When the request signal is received from the irradiation control apparatus 120, the radiation imaging apparatus 101 starts the imaging preparation (TC303). When the imaging preparation is completed (TC304), a signal indicating the completion of the preparation (imaging enabled state) is transmitted from the radiation imaging apparatus 101 to the irradiation control apparatus 120.

Based on the reception of the preparation completion signal that has been transmitted from the radiation imaging apparatus 101, the irradiation control apparatus 120 permits imaging (TC305). If the irradiation button 115 (FIG. 1) is pressed in a state in which the radiation imaging apparatus 101 has not completed the imaging preparation, the radiation irradiation operation is not permitted. When the irradiation button 115 is pressed by the operator in a state in which the radiation imaging apparatus 101 has completed the imaging preparation, the timing control unit 123 of the irradiation control apparatus 120 outputs an irradiation start signal to the radiation generating apparatus 110 so that radiation irradiation will be performed.

The radiation generating apparatus 110 performs radiation irradiation upon receiving the irradiation start signal transmitted from the timing control unit 123 (TC306). The radiation generating apparatus 110 notifies, simultaneously with the radiation irradiation operation, the irradiation control apparatus 120 of the start of the radiation irradiation operation, and notifies, through the network via the network switch 121 of the irradiation control apparatus 120 and the wireless communication unit 103 or the wired communication unit 104 of the radiation imaging apparatus 101, the imaging control unit 102 of the radiation imaging apparatus 101 of the start of the radiation irradiation operation (TC307).

Upon receiving the radiation irradiation start instruction, the imaging control unit 102 of the radiation imaging apparatus 101 makes the radiation imaging apparatus 101 shift from the imaging enabled state to an image obtainment state to obtain a radiation image (TC308).

Upon accepting an irradiation end instruction, the irradiation control apparatus 120 transmits an irradiation end signal from the timing control unit 123 to the imaging control unit 102 of the radiation imaging apparatus 101 (TC309). The transmission of the irradiation end signal is performed through the network via the network switch 121 of the irradiation control apparatus 120 and the wireless communication unit 103 or the wired communication unit 104 of the radiation imaging apparatus 101.

When the irradiation end signal is received, the imaging control unit 102 of the radiation imaging apparatus 101 makes the radiation imaging apparatus 101 shift from the image obtainment state to an image transfer state. The imaging control unit 102 stores a charge accumulation time T1 which is the length of the time taken to obtain the radiation image. The charge accumulation time T1 is the time in which photoelectric conversion was accepted by the image receiver 107 at the time of the obtainment of the radiation image. That is, the charge accumulation time T1 is a time close to the radiation irradiation time.

The imaging control unit 102 transmits the captured radiation image to the control terminal 130 via the wireless communication unit 103 or the wired communication unit 104 and the network switch 121 of the irradiation control apparatus 120. In the control terminal 130, image processing is performed on the transferred image, and display control is performed to cause the display unit 140 to display a preview image to confirm whether a part intended by the operator has been captured, whether imaging needs to be performed again, and the like (TC310).

A time T2 is the time from the start of radiation irradiation until the preview display, and the transfer and image processing of the radiation image are performed in the time T2. The imaging control unit 102 performs processing to thin out the data included in the radiation image at a predetermined ratio to generate a preview image having a data amount smaller than that of the radiation image. The imaging control unit 102 performs display control to display the generated image on the display unit 140.

At TC308, after transferring the image for the display of the preview image, the radiation imaging apparatus 101 shifts to a correction image obtainment operation to generate an image to be used for diagnosis (TC311).

The imaging control unit 102 of the radiation imaging apparatus 101 controls the radiation imaging apparatus 101 to obtain a correction image (a dark current image obtained in a state without radiation irradiation) by the same accumulation time as the accumulation time T1 taken at the obtainment of the radiation image. Note that charge accumulation by a dark current may not be performed in some cases. If the correction image is obtained (TC311), the correction image is transferred from the radiation imaging apparatus 101 to the control terminal 130 via the irradiation control apparatus 120. In response, the display unit 140 generates an image to be used for diagnosis by performing image processing using the already transferred radiation image and the newly transferred correction image, and displays the diagnosis image to the operator (TC312). In this case, a time T3 is the time from the start of radiation irradiation until the display of the diagnosis image, and the transfer of the correction image and image processing using the correction image are performed in the time T3.

In an imaging operation by sequential synchronization as described above, imaging is executed by performing synchronous communication when the radiation imaging apparatus is certainly in an imaging enabled state. Hence, it is applicable to still image capturing which has a low level of requested time accuracy.

(Switching of Synchronous Communication Methods)

Figure 4:
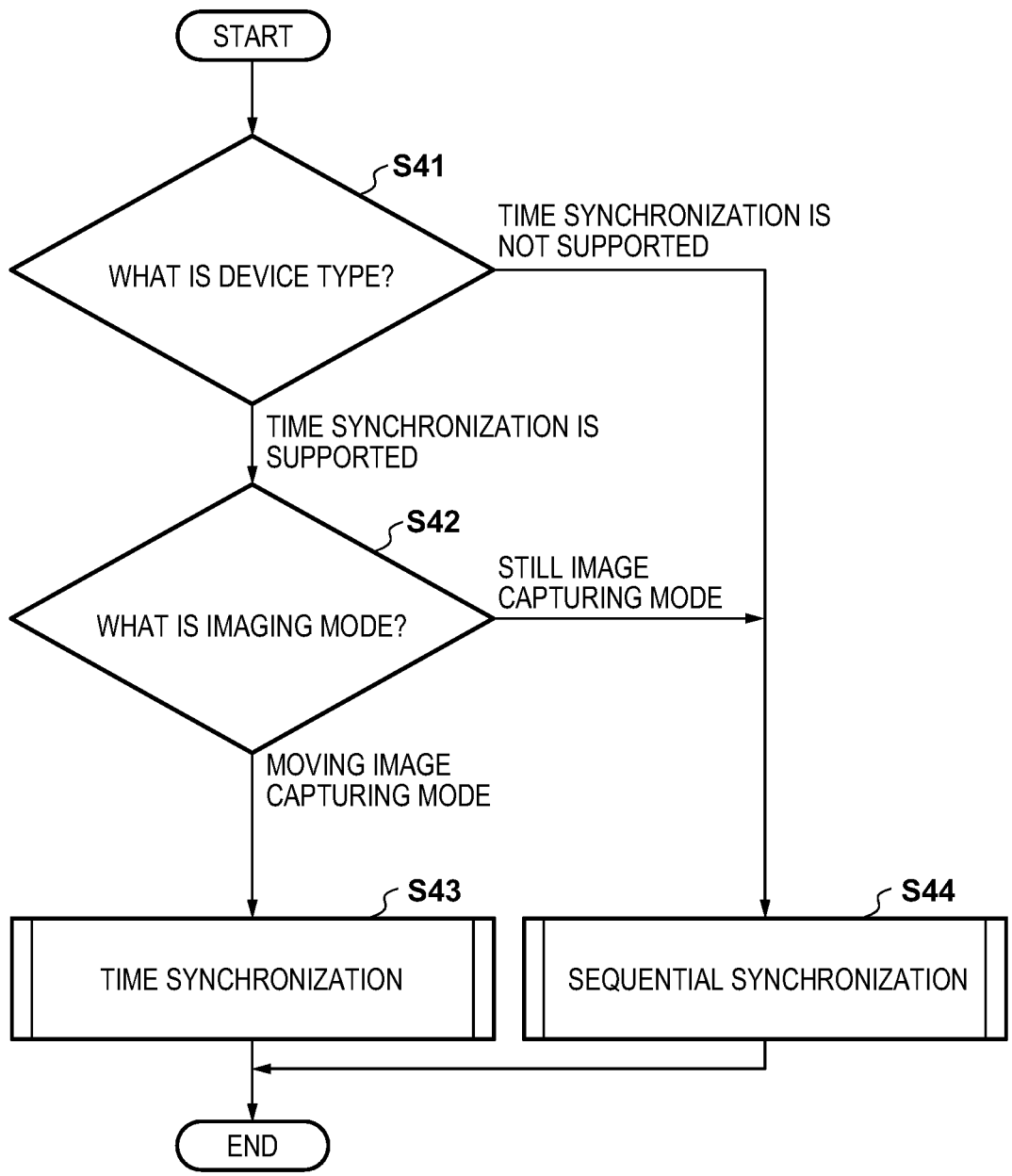
FIG. 4 is a flowchart for explaining the sequence of processing to switch a synchronous communication method (time synchronization or sequential synchronization)

FIG. 4 is a flowchart for explaining the procedure of processing to switch the synchronous communication method (synchronization method). The device type discrimination unit 122 of the irradiation control apparatus 120 determines, based on the identification information set in the radiation imaging apparatus 101, the synchronous communication method that can be supported by the radiation imaging apparatus 101. In this case, the device type discrimination unit 122 can obtain the identification information by communicating with the radiation imaging apparatus 101 or by communicating with a relay apparatus that is used in combination with the radiation imaging apparatus 101.

First, in step S41, the device type discrimination unit 122 of irradiation control apparatus 120 discriminates the device type of the radiation imaging apparatus 101 forming the radiation imaging system. The radiation imaging apparatus 101 has been preset with a few bits of identification information for each synchronization method which can be supported. The device type discrimination unit 122 can obtain the identification information by communicating (communicating via the network switch 121 and the wireless communication unit 103 or the wired communication unit 104) with the radiation imaging apparatus 101. Alternatively, the identification information of the radiation imaging apparatus 101 can be set to the relay apparatus which is used in combination with the radiation imaging apparatus 101, and the device type discrimination unit 122 of the irradiation control apparatus 120 can obtain the identification information by communicating with the relay apparatus.

For example, "001" can be set as the identification information of a device type which can support time synchronization, and "010" can be set as the identification information of a device type that does not support time synchronization. The device type discrimination unit 122 can discriminate the device type of the radiation imaging apparatus 101 based on the identification information obtained from the radiation imaging apparatus 101 via the network switch 121.

If it is determined in step S41 that the device type of the radiation imaging apparatus 101 is a device type that does not support time synchronization, the device type discrimination unit 122 advances the process to step S44 to set sequential synchronization as the synchronization method (S44). On the other hand, if it is determined in step S41 that the device type of the radiation imaging apparatus 101 is a device type that can support time synchronization, the device type discrimination unit 122 advances to the process to step S42.

In step S42, the device type discrimination unit 122 determines the imaging mode (imaging condition) to be executed by the radiation imaging apparatus 101. If it is determined that the still image capturing mode is the imaging mode to be executed by the radiation imaging apparatus 101, the device type discrimination unit 122 advances the process to step S44 and sets sequential synchronization as the synchronization method (step S44).

On the other hand, if it is determined in step S42 that moving image capturing mode is the imaging mode to be performed by the radiation imaging apparatus 101, the device type discrimination unit 122 advances the process to step S43 and sets time synchronization as the synchronization method (step S43).

(Switching of Automatic Detection Mode)

There is an automatic detection mode in which the detection unit 108 of the radiation imaging apparatus 101 detects a current flowing in a bias line of the image receiver 107, and the start and the end of radiation irradiation are detected automatically based on the detection result.

In this case, the automatic detection mode is an operation mode in which the radiation imaging apparatus 101 performs imaging by continuously performing processing for a predetermined time to obtain a radiation image by converting radiation into charges when the radiation imaging apparatus 101 which is in the imaging preparation state has detected radiation irradiation.

Figure 5:
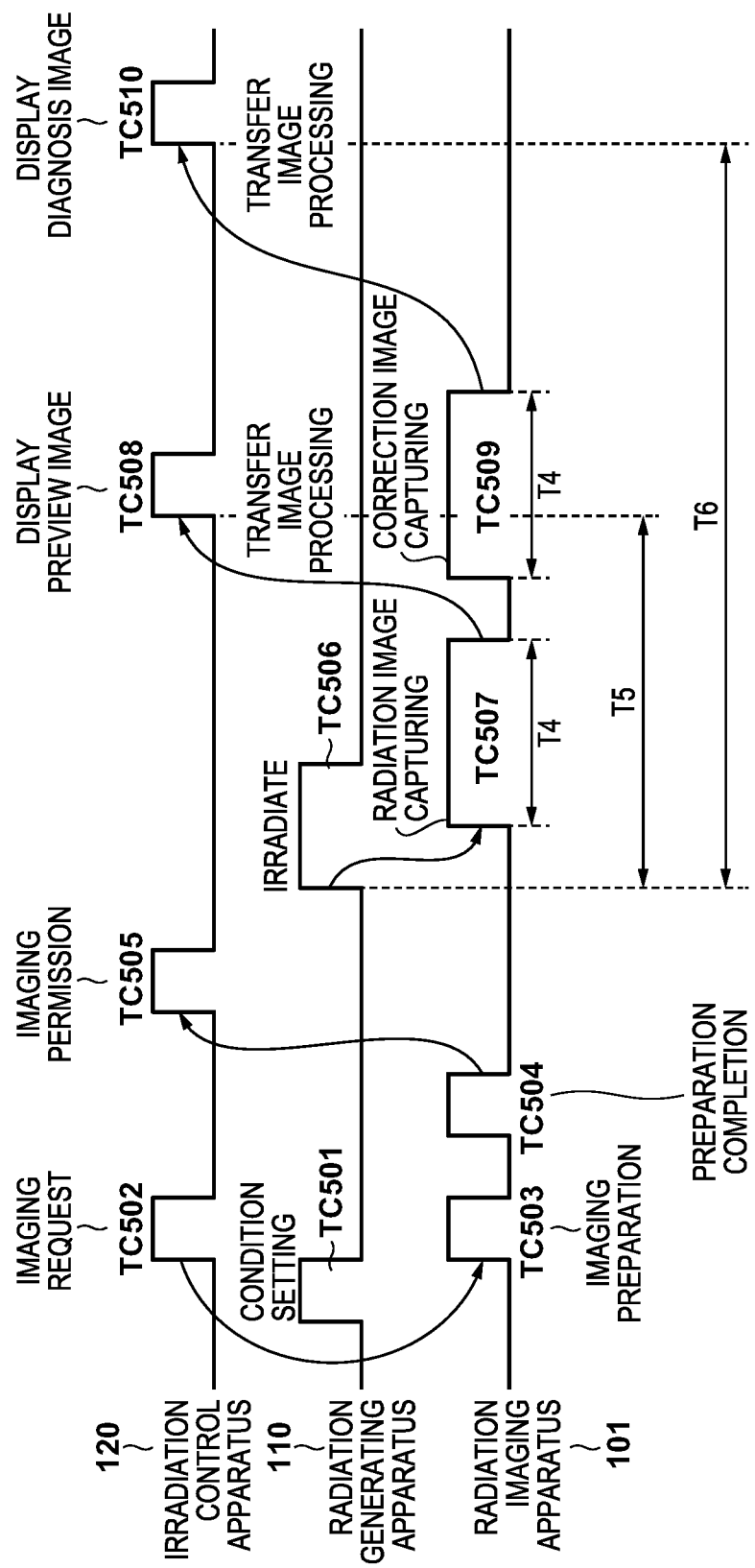
FIG. 5 is a timing chart for explaining the processing procedure of an automatic detection mode.

FIG. 5 is a timing chart for explaining the processing procedure to the automatic detection mode. The outline of an imaging operation by the automatic detection mode will be described with reference to FIGS. 1 and 5.

In FIG. 5, the processes from TC501 to TC505 are the same as the process from TC301 to TC305 described in FIG. 3. It is possible to perform notification so that the operator can confirm that the radiation imaging apparatus 101 is in the imaging preparation completion state.

Upon confirming that the imaging preparation has been completed, the operator presses the irradiation button 115 (FIG. 1), and the irradiation start signal is output to the radiation generating apparatus 110.

The radiation generating apparatus 110 performs radiation irradiation upon receiving the irradiation start signal (TC506). In the sequential synchronization described above, it is arranged so that the radiation generating apparatus 110 will notify, upon executing radiation irradiation, the irradiation control apparatus 120 of the start of the radiation irradiation as well as notify, via the network, the imaging control unit 102 of the radiation imaging apparatus 101 of the start of the radiation irradiation (TC307 of FIG. 3).

On the other hand, in the automatic detection mode, since the radiation imaging apparatus 101 includes the detection unit 108 that detects the execution of radiation irradiation, the irradiation control apparatus 120, the control terminal 130, and the radiation imaging apparatus 101 are not notified of the execution of the radiation irradiation. That is, the device type discrimination unit 122 will determine whether imaging by automatic detection of radiation has been set based on the imaging mode (imaging condition), and the timing control unit 123 will not control the start timing and the end timing of radiation irradiation by the radiation generating apparatus 110 if it is determined, based on the determination result of the device type discrimination unit 122, that the imaging by automatic detection of radiation is set.

In the automatic detection mode, when the detection unit 108 of the radiation imaging apparatus 101 detects radiation irradiation, the detection unit 108 notifies the imaging control unit 102 of the detection result. Based on the detection result of the detection unit 108, the imaging control unit 102 makes the radiation imaging apparatus 101 shift from the imaging enabled state to the image obtainment state to obtain a radiation image (TC507).

In sequential synchronization described above, it is arranged so that the imaging control unit 102 of the radiation imaging apparatus 101 will make the radiation imaging apparatus 101 shift from the image obtainment state to the image transfer state when the irradiation end signal is received (TC309 of FIG. 3).

On the other hand, in the radiation imaging apparatus 101 that has been set to the automatic detection mode, the imaging control unit 102 will control the radiation imaging apparatus 101 to end the obtainment of the radiation image in correspondence with the end of a predetermined accumulation time T4. Although the charge accumulation time T4 for obtaining a radiation image is a predetermined time, a longer period of time, including some extra time, than the general irradiation time (for example, T1 of FIG. 3) will be set as the predetermined time.

When the predetermined accumulation time T4 ends, the imaging control unit 102 makes the radiation imaging apparatus 101 shift from the image obtainment state to the image transfer state.

The imaging control unit 102 transmits the captured radiation image to the control terminal 130 via the wireless communication unit 103 or the wired communication unit 104 and the network switch 121 of the irradiation control apparatus 120. In control terminal 130, image processing is performed on the transferred image, and display control is performed to cause the display unit 140 to display a preview image to confirm whether a part intended by the operator has been captured, whether imaging needs to be performed again, and the like (TC508). A time T5 is the time from the start of radiation irradiation to the preview display, and transferring and image processing of the radiation image are performed in the time T5. The imaging control unit 102 generates a preview image having a smaller data amount than the radiation image by executing processing to thin out the data included in the radiation image at a predetermined ratio. The imaging control unit 102 performs display control to display the generated preview image on the display unit 140.

In TC507, after image transfer has been performed to display the preview image, the radiation imaging apparatus 101 shifts to a correction image obtainment operation to generate an image for diagnosis (TC509). The imaging control unit 102 controls the radiation imaging apparatus 101 to obtain a correction image (a dark current image obtained in a state without radiation irradiation) by the same accumulation time as the accumulation time T4 taken at the obtainment of the radiation image (TC509).

The correction image is transferred from the radiation imaging apparatus 101 to the control terminal 130 via the irradiation control apparatus 120. In response, the display unit 140 generates an image to be used for diagnosis by performing image processing using the already transferred radiation image and the newly transferred correction image, and displays the diagnosis image to the operator (TC510). A time T6 is the time from the start of radiation irradiation until the display of the diagnosis image, and the transfer of the correction image and image processing using the correction image are performed in the time T6.

(Switching of Synchronization Methods and Automatic Detection Mode)

The radiation imaging system 100 can switch, based on the discrimination result by the device type discrimination unit 122, between the synchronization methods (time synchronization and sequential synchronization) and the automatic detection mode.

Figure 6:
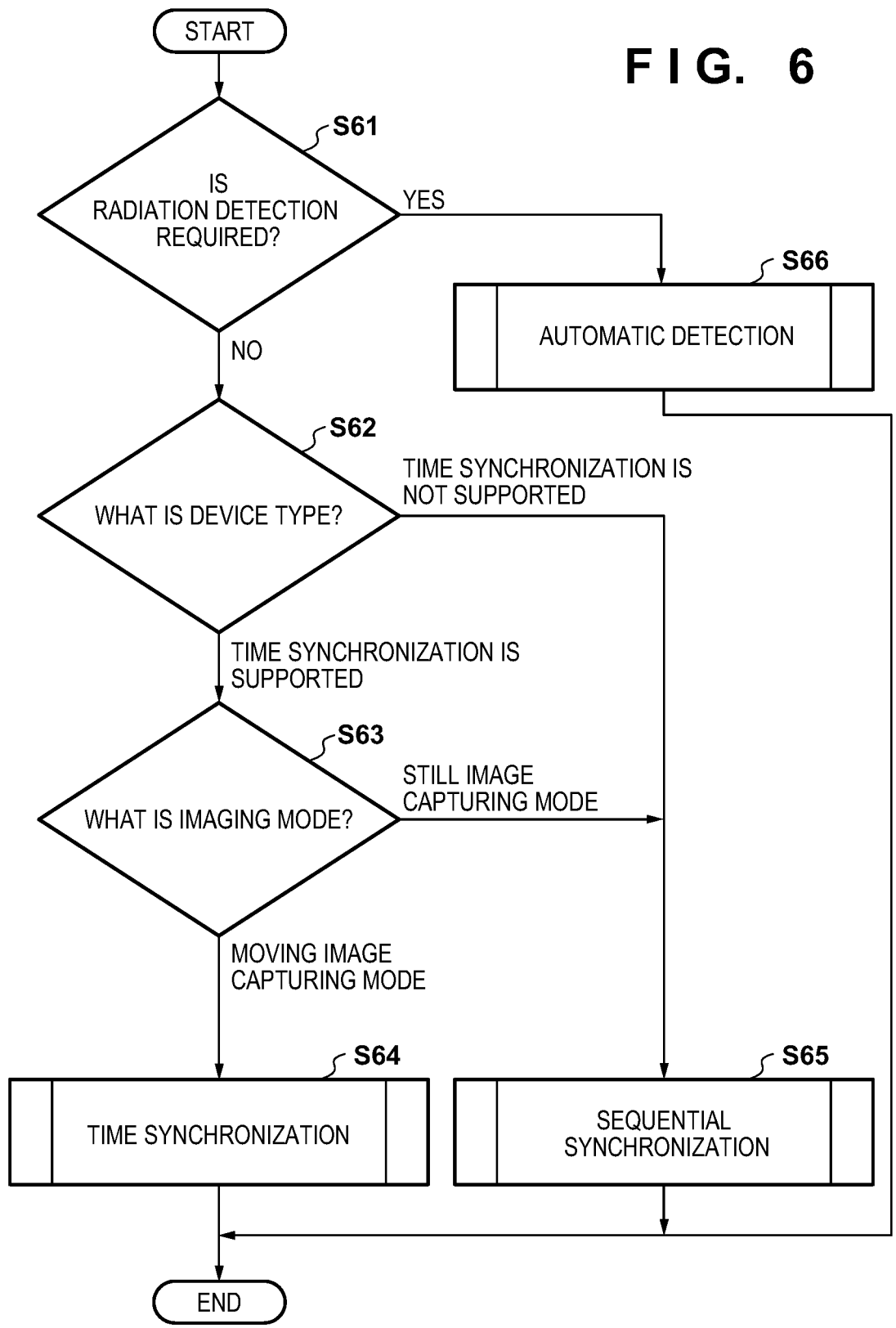
FIG. 6 is a flowchart for explaining processing to switch synchronization including the automatic detection mode.

FIG. 6 is a flowchart for explaining the procedure of the switching processing. First, in step S61, the irradiation control apparatus 120 determines, based on the set imaging mode (imaging condition), whether the imaging setting is a setting that requires automatic detection of radiation. If it is determined that the imaging setting is a setting that requires automatic detection of radiation (YES in step S61), the irradiation control apparatus 120 advances the process to step S66 to set the automatic detection mode (step S66). On the other hand, if it is determined that the imaging setting is not a setting that requires automatic detection of radiation (NO in step S61), the irradiation control apparatus 120 advances the process to step S62.

In step S62, the device type discrimination unit 122 of the irradiation control apparatus 120 discriminates the device type of the radiation imaging apparatus 101 forming the radiation imaging system. The processing for discriminating the device type of the radiation imaging apparatus 101 is the same processing as that of step S41, and the device type discrimination unit 122 can discriminate the device type of the radiation imaging apparatus 101 based on the obtained identification information.

If it is determined in step S62 that the device type of the radiation imaging apparatus 101 is a device type that does not support time synchronization, the device type discrimination unit 122 advances the process to step S65 to set sequential synchronization as the synchronization method (step S65). On the other hand, if it is determined in step S62 that the device type of the radiation imaging apparatus 101 is a device type that supports time synchronization, the device type discrimination unit 122 advances the process to step S63.

In step S63, the device type discrimination unit 122 determines the imaging mode (imaging condition) performed in the radiation imaging apparatus 101. If it is determined that the imaging mode to be performed in the radiation imaging apparatus 101 is the still image capturing mode, the device type discrimination unit 122 advances the process to step S65 to set sequential synchronization as the synchronization method (step S65).

On the other hand, if it is determined in step S63 that the imaging mode to be performed in the radiation imaging apparatus 101 is the moving image capturing mode, the device type discrimination unit 122 advances the process to step S64 to set time synchronization as the synchronization method (step S64).

According to this embodiment, it is possible to provide a radiation imaging technique that allows radiation imaging to be performed by synchronous communication corresponding to the device type of the radiation imaging apparatus. Alternatively, it is possible to provide a radiation imaging technique that allows radiation imaging to be performed by synchronous communication corresponding to the device type and the imaging mode (imaging condition) of the radiation imaging apparatus.

According to this embodiment, it is possible to provide a radiation imaging technique that can control the radiation irradiation timing by a synchronous communication method corresponding to the imaging mode.

In addition, according to this embodiment, power consumption can be reduced by suppressing an excessive amount of communication. Even in a case in which the cooling process of the radiation imaging apparatus is not performed in still image capturing, noise that can be generated in the image can be reduced by suppressing heating by reducing the communication amount.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2019-084428, filed Apr. 25, 2019, which is hereby incorporated by reference herein in its entirety.

What is claimed is:

1. A radiation imaging system comprising an irradiation control apparatus configured to control a timing of radiation irradiation by a radiation generating apparatus and a radiation imaging apparatus configured to communicate by at least one synchronous communication method to synchronize with the radiation irradiation, the irradiation control apparatus comprising:

a determination unit configured to determine an imaging mode that has been set and a synchronous communication method which can be supported by the radiation imaging apparatus; and a control unit configured to control, based on the determination result, the timing of the radiation irradiation by a synchronous communication method corresponding to the imaging mode, wherein the synchronous communication method includes a time synchronization method in which communication is performed to match (i) a time of an internal timer included in the irradiation control apparatus and (ii) a time of an internal timer included in radiation imaging apparatus, and in which radiation irradiation is performed based on the time of the internal timer included in the irradiation control apparatus, and a driving timing of an image receiver is controlled based on the time of the internal timer included in the radiation imaging apparatus, and the synchronous communication method further includes a sequential synchronization method in which the control unit outputs an imaging permission that allows radiation irradiation to be performed, after imaging preparation has been completed in the radiation imaging apparatus in response to an imaging request from the irradiation control apparatus.

2. The system according to claim 1, wherein the control unit is configured to switch communication with the radiation imaging apparatus based on the determination result.

3. The system according to claim 1, wherein the determination unit is configured to determine, based on the imaging mode, whether a setting to perform imaging by automatic detection of radiation is set, and if the determination result determines that the setting to perform imaging by the automatic detection of radiation is set, the control unit is configured not to control a start timing and an end timing of the radiation irradiation by the radiation generating apparatus.

4. The system according to claim 1, wherein the imaging mode includes moving image capturing and still image capturing, and the control unit is configured to control the timing of the radiation irradiation by the time synchronization in the moving image capturing, and to control the timing of the radiation irradiation by the sequential synchronization in the still image capturing.

5. The system according to claim 1, wherein the determination unit is configured to determine the synchronous communication method that can be supported by the radiation imaging apparatus based on identification information set to the radiation imaging apparatus, and the identification information is obtained by one of communication with the radiation imaging apparatus and communication with a relay apparatus which is used in combination with the radiation imaging apparatus.

6. The system according to claim 1, wherein the radiation imaging apparatus comprises:

a communication unit configured to obtain time information of the irradiation control apparatus by exchanging a message with the irradiation control apparatus; and a time control unit configured to synchronize time information of an internal timer with the time information of the irradiation control apparatus.

7. The system according to claim 6, wherein the time control unit is configured to estimate a reply time at which the irradiation control apparatus transmitted the reply message based on an inquiry transmission time of the message and a reply reception time at which a reply message to the message is received from the irradiation control apparatus.

8. The system according to claim 7, wherein a reply transmission time at which the irradiation control apparatus transmitted the reply message is stored in the reply message.

9. The system according to claim 8, wherein the time control unit is configured to obtain a correction value of the time from a difference time between the estimated reply time and the reply transmission time to correct the time information of the internal timer by the correction value.

10. A radiation control apparatus configured to control a timing of radiation irradiation by a radiation generating apparatus and to communicate with a radiation imaging apparatus by at least one synchronous communication method to synchronize with the radiation irradiation, comprising:

a determination unit configured to determine an imaging mode that has been set and a synchronous communication method which can be supported by the radiation imaging apparatus; and a control Unit configured to control, based on the determination result, the timing of the radiation irradiation by a synchronous communication method corresponding to the imaging mode, wherein the synchronous communication method includes a time synchronization method in which communication is performed to match (i) a time of an internal timer included in the irradiation control apparatus and (ii) a time of an internal timer included in radiation imaging apparatus, and in which radiation irradiation is performed based on the time of the internal timer included ii the irradiation control apparatus, and a driving timing of an image receiver is controlled based on the time of the internal timer included in the radiation imaging apparatus, and the synchronous communication method further includes a sequential synchronization method in which the control unit outputs an imaging permission that allows radiation irradiation to be performed, after imaging preparation has been completed in the radiation imaging apparatus in response to an imaging request from the irradiation control apparatus.

11. A method of controlling a radiation imaging system that comprises an irradiation control apparatus configured to control the timing of radiation irradiation by a radiation generating apparatus and a radiation imaging apparatus configured to communicate by at least one synchronous communication method to synchronize with the radiation irradiation, the method comprising the steps of:

determining an imaging mode that has been set and a synchronous communication method which can be supported by the radiation imaging apparatus, and controlling, based on a result from the determining, the timing of the radiation irradiation by a synchronous communication method corresponding to the imaging mode, wherein the synchronous Communication method includes a time synchronization method in which communication is performed to match (i) a time of an internal timer included in the irradiation control apparatus and (ii) a time of an internal timer included in radiation imaging apparatus, and in which radiation irradiation is performed based on the time of the internal timer included in the irradiation control apparatus, and a driving timing of an image receiver is controlled based on the time of the internal timer included in the radiation imaging apparatus, and the synchronous communication method further includes a sequential synchronization method in which the control unit outputs an imaging permission that allows radiation irradiation to be performed, after imaging preparation has been completed in the radiation imaging apparatus in response to an imaging request from the irradiation control apparatus.

\* \* \* \* \*